United States Patent [19]
Millner et al.

[11] Patent Number: 5,302,643
[45] Date of Patent: Apr. 12, 1994

[54] CLARIFIERS FOR POLYOLEFINS AND POLYOLEFIN COMPOSITIONS CONTAINING SAME

[75] Inventors: O. Elmo Millner, Durham; Richard P. Clarke; George R. Titus, both of Raleigh, all of N.C.

[73] Assignee: Becton, Dickinson and Company, Franklin Lakes, N.J.

[21] Appl. No.: 96,284

[22] Filed: Jul. 26, 1993

Related U.S. Application Data

[62] Division of Ser. No. 545,161, Jun. 28, 1990.

[51] Int. Cl.$^5$ .................... C08K 5/15; C08L 23/00; C08L 23/12
[52] U.S. Cl. ................... 524/109; 524/570; 524/582
[58] Field of Search .............. 524/109, 570, 582

[56] References Cited

U.S. PATENT DOCUMENTS

| | | | |
|---|---|---|---|
| 4,016,118 | 4/1977 | Hamada et al. | 524/108 |
| 4,371,645 | 2/1983 | Mahaffey, Jr. | 524/108 |
| 4,483,952 | 11/1984 | Uchiyama | 524/108 |
| 4,808,650 | 2/1989 | Titus et al. | 524/108 |
| 4,845,137 | 7/1989 | Williams et al. | 524/108 |

FOREIGN PATENT DOCUMENTS 60-081257  5/1985  Japan.

*Primary Examiner*—Joseph L. Schofer
*Assistant Examiner*—Wu C. Cheng
*Attorney, Agent, or Firm*—Richard E. Brown

[57] ABSTRACT

Dibenzylidene xylonates are a new class of clarifiers for polyolefins. The invention includes polyolefin compositions having the new clarifiers therein.

4 Claims, No Drawings

CLARIFIERS FOR POLYOLEFINS AND POLYOLEFIN COMPOSITIONS CONTAINING SAME

This is a division of application Ser. No. 07/545,161, filed Jun. 28, 1990.

BACKGROUND OF THE INVENTION

1. Field of the Invention

This invention relates to polyolefin compositions of improved clarity and, more particularly and in addition thereto, relates to a new class of additives which confer improved clarity to polyolefins.

2. Background of the Invention

For many applications, polymeric products have been fabricated into structural or block forms, such as fibers, which utilize properties based on their high molecular weights. In recent years, applications have been developed, such as plates, sheets, films and the like, in which clarity or transparency is a very desirable property. Clarity is also very important for certain plastic articles, such as syringes, made by injection molding.

In general, clarity is not an inherent property of polyolefin plastics, most of which are more or less opaque due principally to their partially amorphous nature. Most polyolefins do, however, have some crystallinity, and they are generally referred to as semicrystalline. High clarity is thought to be related crystal size. Large crystals reduce clarity, an effect generally thought to be due to diffraction and scattering of light, and most polyolefins of good clarity are predominantly microcrystalline.

Various additives for polyolefins, conventionally referred to as nucleators, which promote crystallization at many sites, have been disclosed. These additives are derivatives of sorbitol. U.S. Pat. No. 4,016,118 to Hamada et al. teaches improved clarity and resistance to mold shrinkage in polyolefins containing from about 0.1% to 0.7% of dibenzylidene sorbitol. This product has dominated the commercial clarifier market since its introduction. Other dibenzylidene sorbitol clarifying additives postulated to function by reducing crystal size are disclosed in U.S. Pat. No. 4,371,645 to Mahaffey and U.S. Pat. No. 4,483,952 to Uchiyama. In the former patent, the phenyl rings are substituted with at least one halogen atom, and may additionally have alkyl, hydroxy, methoxy, amino or nitro substituent groups. The dibenzylidene sorbitols of the latter patent have chloro, alkyl or alkoxy substituents in each of the phenyl rings. Dibenzylidene sorbitol clarifiers having fluorine and sulfur substituents are disclosed as having improved clarity in U.S. Pat. Nos. 4,808,650 and 4,845,137 respectively.

SUMMARY OF THE INVENTION

Dibenzylidenexylonic acids and derivatives thereof are clarifiers for polyolefins. Preferred clarifiers have a substituent on the aromatic ring, such as an alkyl, thioalkyl, alkoxy or halogen. The most preferred clarifiers have a methyl group in the 4 and 4' positions. Preferred derivatives are esters, amides, hydrazides, hydroxylamides and amidines.

The clarifiers may be compounded into the polyolefin at very low concentrations, preferably about 0.1 to 0.5% by weight.

Thus the invention provides a new class of clarifying agents and polyolefin compositions which have the clarifier incorporated therein. In addition, significant advantages with respect to production costs are also realized with the additives of the present invention. Because high clarity compositions are achieved with as little as 0.10% of the additives, the total additive package required per batch of polyolefin composition is reduced, resulting in cost savings. Further, since the additives of the invention increase the temperature at which a polyolefin composition in a mold crystallizes, the mold can be opened sooner to remove the contents. The reduced "mold time" provides a savings in time which is translated into a cost saving because the mold can produce more units of product in a given period of time.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

High clarity polyolefins have found application in recent years in the form of films, particularly in the food packaging industry. In addition, they are often used in disposable medical and laboratory devices, such as syringe barrels and pipets where clarity is an aid for visualization and also provides aesthetic qualities. Most clarified polyolefins are used in the 30 to 50 mil thickness range.

The polyolefin component of the composition of the present invention having high clarity and high resistance to oxidative degradation may be a homopolymer or copolymer of an aliphatic monolefin, preferably with 2 to 6 carbon atoms, having a number average molecular weight of about 10,000 to 200,000, preferably about 30,000 to 150,000. The polyolefins of the present invention may be described as basically linear, but may optionally contain side chains such as are found, for instance, in conventional, low density polyethylene. Exemplary of such polyolefins are polyethylene, polymethylpentene, polytetrafluoroethylene and the like. The preferred polyolefin is polypropylene.

The polyolefin may contain a small amount, generally from 1 to 10 percent of an additional polymer incorporated into the composition by copolymerization with the appropriate monomer. Such copolymers may be added to the composition to enhance other characteristics of the final composition, and may be, for example, polyacrylate, polyvinyl, polystyrene and the like.

The additives having clarifying properties of the present invention are xylonic acid derivatives consisting substantially of dibenzylidene xylonic acid derivatives of the following general structure:

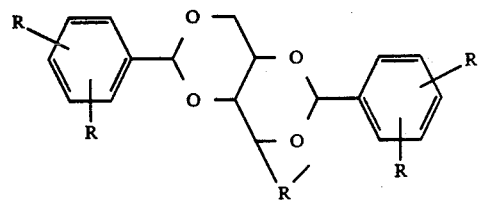

wherein R may be hydrogen, halogen, lower alkoxy, lower alkyl, lower alkenyl, phenyl, lower alkylthio, or phenylthio, and R' may be a carboxyl group or a carboxyl derivative. Representative non-limiting examples of useful carboxyl derivatives are amides, hydrazides, hydroxylamides, amidines and alkyl substituted derivatives thereof. The term lower with respect to alkyl or alkoxy is intended to be from 1 to 6 carbon atoms, branches or unbranched.

The additives of the invention may be prepared by any suitable sequence of reactions as known in the art. In one method, the known dibenzylidene xylonic acid may be converted by conventional chemistry to various acid derivatives. A particularly convenient method is acid-catalyzed condensation of the appropriate substituted benzaldehyde with ammonium xylonate. The stoichiometry of this reaction is two moles of aldehyde per mole of xylonate, and while the preferred ratio of these reactants is at or close to 2:1, other ratios deviating from this preferred value, but still suitable for preparation of the additives, are readily apparent to one ordinarily skilled in the art. Likewise, selection of suitable solvents, acid catalysts, reaction conditions, workup conditions and product isolation procedures are well within the purview of one skilled in the art. Representative suitable and non-limiting aldehydes are benzaldehyde, 4-methylbenzaldehyde, 3,4-dimethylbenzaldehyde, 4-chlorobenzaldehyde, 3-methoxybenzaldehyde, 4-methylthiobenzaldehyde, and 4-biphenylcarboxaldehyde.

Condensation of a benzaldehyde and a xylonate under the above conditions leads predominately to the dibenzylidene derivative of the invention. It is appreciated, however, that by-product monobenzylidene derivatives will also be formed, the quantity of the by-products formed being variable depending on the reaction workup and purification procedures. In general, it is not necessary to remove these by-products because the clarifying effectiveness of the dibenzylidene xylonates of the invention is not substantially decreased by the presence of the by-products. It is preferred, however, that the additive of the invention consist of 90% or higher of the dibenzylidene xylonate additive. As known in the art, monobenzylidene by-products may be removed by recrystallization from a suitable solvent. Such purification techniques are routine and well-known to those skilled in the art.

Clarifying properties are conferred when the additive of the invention is formulated into the polyolefin composition in a quantity within the range of about 0.005 to 2.0% by weight. Higher percentages of additives may be used but generally provide no perceived advantage. The preferred concentration range may be from about 0.05 to 0.5%, most preferably, from about 0.1% to 0.3%.

Other additives as known in the art may be added to provide other desirable properties to the composition. For example, fillers, coloring agents, plasticizers, antistatic materials, wetting agents and the like may be added in suitable quantities providing no deleterious effects in the desired clarity or mechanical strength are introduced. In addition, other known clarifying additives, as for example, organic acids and metal salts thereof, such as para-t-butylbenzoic acid, may be incorporated into the composition.

Preparation of the composition of the invention from its constituent parts is routine and may be carried out by any conventional mixing means.

Clarity of a polyolefin composition is conventionally reported as the haze value. Haze values of the compositions of the invention may be determined in accordance with ASTM procedure D 1003. In Table I, representative polypropylene-additive compositions of the invention and their haze values are shown and compared with clarifier compositions containing dibenzylidene sorbitol, the clarifier most widely used commercially.

TABLE 1

| Polypropylene Additive | Concentration (Wt %) | Haze (%) Sample = 0.040" |
|---|---|---|
| None | — | 66.8 |
| Dibenzylidene sorbitol | 0.10 | 60 |
|  | 0.20 | 24 |
|  | 0.40 | 22 |
| Dibenzylidene xylonic acid | 0.10 | 31.9 |
|  | 0.20 | 33.3 |
|  | 0.40 | 32.4 |
| 4,4'-dimethyldibenzylidene xylonic acid hydoxylamide | 0.1 | 52.8 |
|  | 0.2 | 47.8 |
| 4,4'-dimethyldibenzylidene xylonic acid hydrazide | 0.1 | 40.2 |
|  | 0.2 | 25.4 |
|  | 0.4 | 34.6 |
| 4,4'-dimethyldibenzylidene xylonic acid methyl hydrazide | 0.1 | 59.2 |
|  | 0.2 | 40.8 |
|  | 0.4 | 23.4 |
| 4,4'-dimethyldibenzylidene methyl xylonate | 0.1 | 56.0 |
|  | 0.2 | 50.2 |
|  | 0.4 | 52.8 |

The following examples are provided to further illustrate the invention but are not to be considered as limitative of the invention.

EXAMPLE I

Preparation of Ammonium Xylonate

Calcium xylonate, 3.70 g (0.01 mol) was dissolved in 40 ml water. While stirring at 40° C., a solution of 1.06 g (0.011 mol) ammonium carbonate in 5 ml water was added, the mixture allowed to stand 4 hours at room temperature and filtered to remove the calcium carbonate. The aqueous solution was decolorized with activated charcoal, filtered, and evaporated at 40° C. under vacuum to afford a syrup which crystallized on standing. The crystals were slurried in 20 ml MeOH, filtered, and washed again with MeOH on the filter. The product was dried in vacuo over $P_2O_5$ to afford 2.45 g (67%). The prisms obtained had MP=118° to 122° C., LIT=120° to 122° C. (Carbohyd. Res. 7 (1968) 38–55).

EXAMPLE II

Preparation of 4,4'-Dimethyl Dibenzylidene Xylonic Acid

Ammonium xylonate (1.83 g, 0.01 mol) was mixed with 15 ml 4-methylbenzaldehyde and 2.0 ml conc HCl for 8 hours at ambient temperature. Subsequently, the reaction mixture was neutralized with 5% sodium carbonate solution to pH=8 and excess 4-methylbonzaldehyde was removed by extraction with ether (3×50 ml). The aqueous phase was extracted twice with 40 ml $CHCl_3$, then with 80 ml warm chloroform (60° C.). The chloroform extracts were combined and washed with 2N HCl. The 2N HCl phase was extracted with $CHCL_3$ (3×40 ml). All of the chloroform extracts were combined, washed with warm water (60° C.) (2×100 ml), dried over sodium sulfate, and evaporated to obtain a crystalline residue. The product was recrystallized from methanol and dried at 100° C. overnight, m.p. 205° to 8° C. (d).

In the same way as described above, use of the appropriate benzaldehydes gave the following dibenzylidene xylonic acids:
1) dibenzylidene xylonic acid, mp. 198° to 200° C.
2) 4,4-dichlorodibenzylidene xylonic acid, mp. 221° to 224° C.

EXAMPLE III

Preparation of 4,4'-Dimethyl Dibenzylidene Xylonic Acid Methyl Ester

Ammonium xylonate (9.88 g, 0.054 mol), prepared as described in Example I, was dissolved in 100 ml of water and warmed to 40° C. A solution of 4-methylbenzaldehyde (30.0 g, 0.25 mol) in 200 ml methanol containing concentrated HCl (10.0 ml) was then added to the aqueous xylonate solution. The new solution was then heated at reflux for four hours with constant stirring. On cooling, a large volume of colorless crystalline product precipitated. These were recovered by filtration, washed with methanol (2×100 ml) and dried in vacuo to afford the methyl ester (16.0 g, 0.042 mol), m.p. 269°-271° C.

EXAMPLE IV

Preparation of 4,4'-Dimethyl Dibenzylidene Xylonic Acid Hydrazides

The product fro Example III (1.0 g) was slurried in 100 ml of methanol containing 10 ml of hydrazine. The mixture was heated for one hour at 65° C., then poured into water. The precipitated hydrazide was filtered, mp. 220°-30° C. (d).

In the same way, the methyl hydrazide was prepared from methyl hydrazine, mp. 225°-35° C. (d).

EXAMPLE V

Preparation of 4,4'-Dimethyl Dibenzylidene Xylonic Acid Hydroxylamide

The methyl ester (10.0 g; 0.026 mol), prepared as described in Example III, was slurried in 400 ml pyridine. Hydoxylamine hydrochloride (25 g, 0.36 mol) and potassium hydroxide (25 g, 0.38 mol) were stirred ether in 800 ml methanol for 15 minutes and then filtered. The methanolic solution of hydroxylamine was rapidly added to the previously prepared pyridine slurry. The new slurry was heated to 65° C. overnight and the resulting solution was then cooled to ambient temperature. Concentrated HCl (30 ml) in 500 ml water was added to induce precipitation of the product. A colorless solid was collected by filtration, washed with water (2×200 ml), washed with methanol (2×200 ml), and dried in vacuo. The product (4.4 g, 0.011 mol) was an off-white solid, m.p. 229° to 234° C.

EXAMPLE VI

Polypropylene (500 g), obtained in pellet form from the manufacturer, was shaken with 4,4'-dimethyl dibenzylidene xylonate (2.5 g, finely powdered) to coat the pellets electrostatically. The pellets were then extruded through a single screw extruder at 210° C., cooled in a water bath, and re-pelletized.

The new pellets were then molded into step plaques 50×75 mm in overall dimension by injection molding. The upper step was 0.080 inches thick while the lower step was 0.040 inches thick. The haze values reported in Table I were measured using ASTM Method D1003 using a 0.04 inch step and are the average of 5 readings.

Thus, in accordance with the invention, there is provided new polyolefin compositions of high clarity which result from inclusion of new dibenzylidene xylonate additives. In addition to clarity, savings in production costs are achieved because high clarity is achieved with very low percentages of additive, and because the compositions of the invention have a higher crystallization temperature giving reduced mold times.

What is claimed is:

1. A composition comprising a polyolefin and a clarifying amount of an additive of the structure

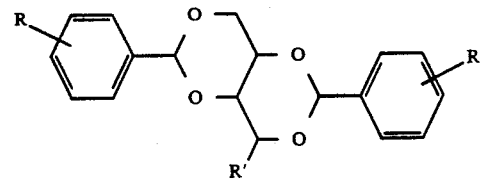

wherein R is selected from the group consisting of halogen and lower alkyl of 1 to 6 carbon atoms, and R¹ is selected from the group consisting of carboxyl and a carboxyl derivative.

2. The composition of claim 1 wherein said polyolefin is selected from the group consisting of polyethylene, polypropylene, polymethylpentene and polytetrafluoroethylene.

3. A composition comprising a polyolefin and clarifying amount of an additive of the structure

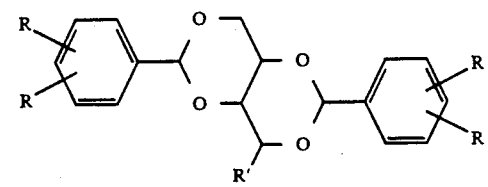

wherein R is selected from the group consisting of halogen, lower alkoxy, lower alkyl, lower alkenyl, phenyl, lower alkylthio and phenylthio the term lower meaning from 1 to 6 carbon atoms, and R¹ is selected from the group consisting of carboxyl and carboxyl derivative.

4. A composition comprising polypropylene and a clarifying amount of an additive of the structure

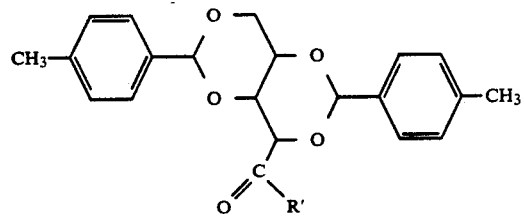

wherein R' is selected from the group consisting of a hydroxyl, alkoxyl, amino, hydroxylamino, hydrazino and a lower alkyl substituted amino and hydrazino of 1 to 6 carbon atoms.

* * * * *